United States Patent
Albitar

(10) Patent No.: US 10,550,435 B2
(45) Date of Patent: Feb. 4, 2020

(54) DETERMINING TUMOR LOAD AND BIALLELIC MUTATION IN PATIENTS WITH CALR MUTATION USING PERIPHERAL BLOOD PLASMA

(71) Applicant: NeoGenomics Laboratories, Inc., Fort Myers, FL (US)

(72) Inventor: Maher Albitar, Valley Center, CA (US)

(73) Assignee: NEOGENOMICS LABORATORIES, INC., Fort Myers, FL (US)

( * ) Notice: Subject to any disclaimer, the term of this patent is extended or adjusted under 35 U.S.C. 154(b) by 0 days.

(21) Appl. No.: 14/937,942

(22) Filed: Nov. 11, 2015

(65) Prior Publication Data

US 2016/0130664 A1 May 12, 2016

Related U.S. Application Data

(60) Provisional application No. 62/083,435, filed on Nov. 24, 2014, provisional application No. 62/078,953, filed on Nov. 12, 2014.

(51) Int. Cl.
| | | |
|---|---|---|
| *C12Q 1/68* | (2018.01) | |
| *C12Q 1/6886* | (2018.01) | |
| *A61N 5/10* | (2006.01) | |

(52) U.S. Cl.
CPC .............. *C12Q 1/6886* (2013.01); *A61N 5/10* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2013/0129668 A1 | 5/2013 | Firestein et al. |
| 2014/0274740 A1 | 9/2014 | Srinivasan et al. |
| 2015/0079091 A1 | 3/2015 | Kralovics et al. |
| 2018/0148756 A1 | 5/2018 | So et al. |

FOREIGN PATENT DOCUMENTS

| | | |
|---|---|---|
| WO | WO 2013159035 | 10/2013 |
| WO | 2014068072 A1 | 5/2014 |
| WO | 2014130890 A1 | 8/2014 |

OTHER PUBLICATIONS

Cervantes et al; Blood, vol. 113, 2009; pp. 2895-2901.*
Middendorf et al; Essentials of Genomics and Bioinformatics; John Wiley & Sons, 2008; Chapter 8, pp. 1-16.*
Mussolin et al; Journal of Cancer, 2013, vol. 4, pp. 323-329.*
Elshimali et al; Int. J. Mol. Sci. 2013; vol. 14,pp. 18925-18958.*
Nanglia J., et al., Somatic CALR Mutations in Myeloproliferative Neoplasms with Non-mutated JAK2, New England J. Med., Dec. 19, 2013: 369(25), 2391-2405.
Malcovati L. et al., Somatic Mutations of Calreticulin in Myeloproliferative Neoplasms and Myelodysplastic/Myeloproliferative Neoplasms, Haematologica, 2014, 99(11), 1650-1652.
Klampfl, T. Ph.D. et al., Somatic Mutations of Calreticulin in Myeloproliferative Neoplasms, The New England Journal of Medicine, Dec. 19, 2013, 369(25), 2379-2390.
Chi, J. et al., "Calreticulinmutations in myeloproliferative neoplasms and new methodology for their detection and monitoring"; Annals of Hematology, Berlin DE; Oct. 29, 2014; pp. 399-408; vol. 94, No. 3.
Diep, K. et al., "Determining Tumor Load and Ballellic Mutation in Patients with CALR Mutation Using Peripheral Blood Plasma | Blood Journal" ; Blood; Dec. 6, 2014; 4 pages; 124:1818.
EP15858528.1 Supplementary European Search Report and European Search Opinion dated May 9, 2018, 9 pages.
Wu, Z. et al.; "The mutation profile of JAK2 and CALR in Chinese Han patients with Philadelphia chromosome-negative myeloproliferative neoplasms"; Journal of Hematology & Oncology, Biomed Central Ltd, London UK, Jul. 15, 2014; vol. 7, No. 1, p. 48.

* cited by examiner

*Primary Examiner* — Jehanne S Sitton
(74) *Attorney, Agent, or Firm* — Eleanor Musick; Musick Davison LLP

(57) ABSTRACT

Compositions and fragment length analysis methods are provided for detecting CALR mutations and determining tumor load in patients with myeloproliferative neoplasms.

19 Claims, 2 Drawing Sheets

Specification includes a Sequence Listing.

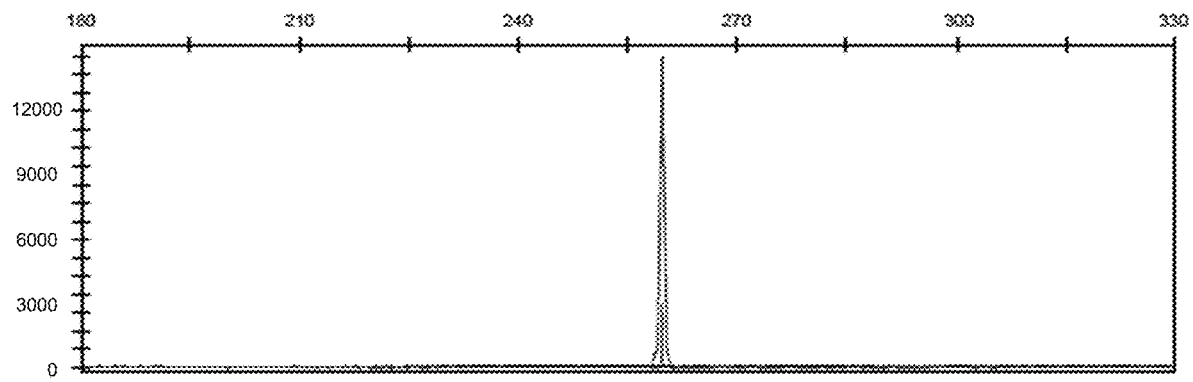
FIG. 1A  Normal
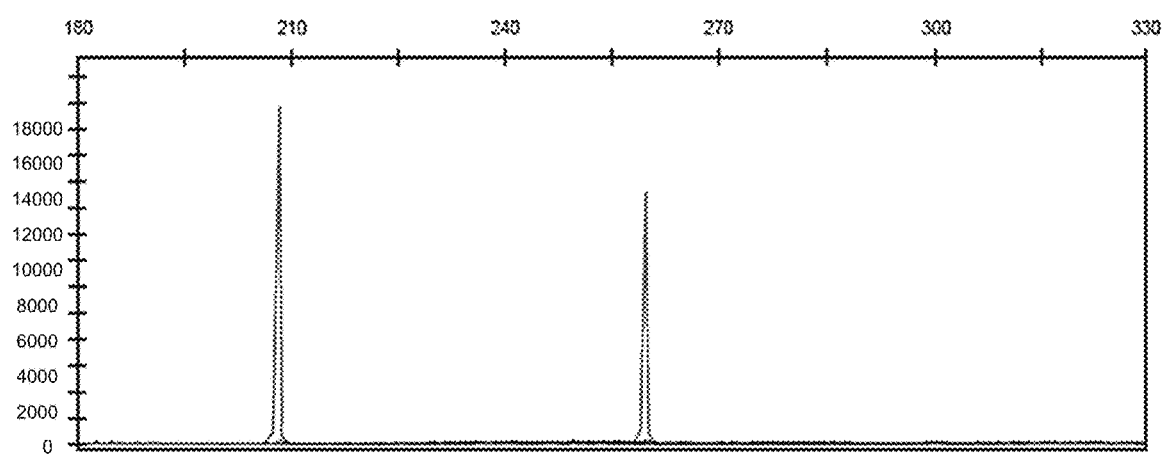
FIG. 1B  Biallelic, similar mutations
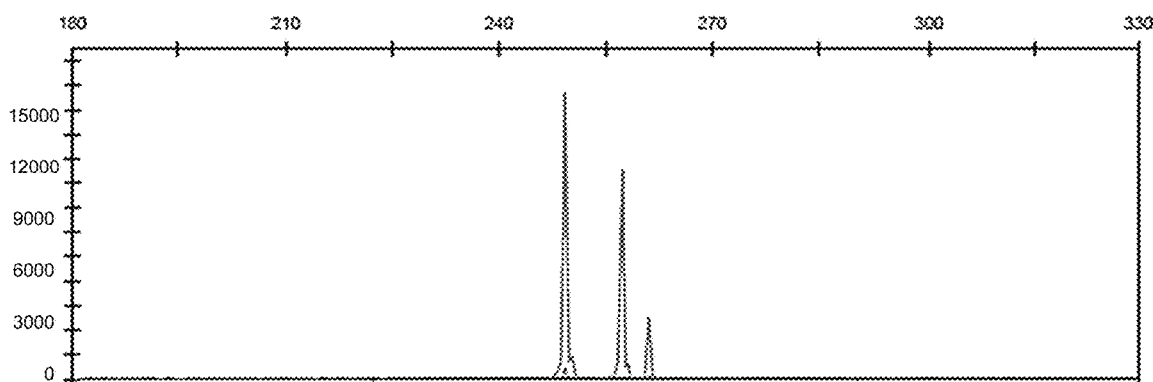
FIG. 1C  Biallelic, different mutations

DETERMINING TUMOR LOAD AND BIALLELIC MUTATION IN PATIENTS WITH CALR MUTATION USING PERIPHERAL BLOOD PLASMA

CROSS-REFERENCE TO RELATED APPLICATION

This application claims the benefit of priority from U.S. Provisional Patent Application 62/078,953 filed Nov. 12, 2014 and U.S. Provisional Patent Application 62/083,435 filed Nov. 24, 2014, the entire disclosures of which are incorporated herein by reference.

TECHNICAL FIELD

This invention provides compositions and methods for diagnosing, monitoring and managing myeloproliferative neoplasms.

BACKGROUND

Myeloproliferative neoplasms (MPNs) are chronic myeloid cancers that are characterized by the overproduction of mature blood cells, and that may evolve into acute myeloid leukemia. In addition to chronic myeloid leukemia with the BCR-ABL fusion gene, the three most common myeloproliferative neoplasms are essential thrombocythemia, polycythemia vera, and myelofibrosis.

Chronic myeloproliferative neoplasms (MPNs) are diagnosed and confirmed by morphologic and characteristic molecular abnormalities. Almost all cases with polycythemia vera (P-Vera) are characterized by a mutation in JAK2. Primary myelofibrosis (PMF) and essential thrombocythemia (ET) show JAK2 mutation in 40% of cases and MPL gene mutation in 2% of cases. Tests for these JAK2 mutations have greatly simplified the diagnosis of MPNs and are part of the standard screening mechanisms. However, distinguishing essential thrombocythemia with non-mutated JAK2 from the more common reactive thrombocytosis remains a diagnostic challenge.

Additional mutations have been identified in patients who have MPNs with or without JAK2 mutations, but these additional mutations affect only a small number of patients. Recently, researchers have identified the gene encoding calreticulin (CALR) as a new cancer gene that is frequently mutated in patients with MPNs. (J. Nanglia, et al., "Somatic CALR mutations in myeloproliferative neoplasms with non-mutated JAK2", *New England J. Med.*, Dec. 19, 2013: 369(25): 2391-2405). The recently discovered calreticulin (CALR) mutation is reported in 67% of ET cases and 88% of PMF that lack JAK2 or MPL gene mutations.

Somatic mutations in the calreticulin gene CALR are detected in peripheral blood in the ~65-85% of essential thrombocythemia (ET) and primary myelofibrosis (PMF) patients that are JAK2- and MPL-mutation negative. Molecular analysis of these three genes now allows these disease markers to be identified in >90% of MPN patients, helping to classify the disease and differentiate it from a reactive process. CALR mutation testing also has prognostic value as CALR mutations are associated with longer survival and fewer thrombotic events compared to JAK2 mutations.

Calreticulin is a calcium-binding protein involved in signaling and protein expression that is believed to be responsible for clearing misfolded proteins and involved in expression regulation. CALR mutations reported in myeloproliferative neoplasms create translation frameshifts in exon 9 which truncate the C-terminal calcium binding domain and create a novel C-terminal peptide. CALR mutations are insertions or deletions in exon 9 and highly unlikely to be missense mutation. The two most common mutations in CALR are 52-bp deletions (type 1 mutation) and 5-bp deletions (type 2 mutation). Respectively, they have been shown to account for approximately 53% and 31.7% of detected CALR mutations. Initial reports support CALR mutations as early and disease-initiating mutations that favor expansion of the megakaryocytic lineage. CALR mutations are mutually exclusive with JAK2 or MPL mutations.

Almost all mutations involve both insertions and deletions ("indel")—some with large (>50 bp) deletion. Detecting this type of mutation with acceptable sensitivity is difficult to achieve using conventional sequencing techniques.

Allele burden has been shown to play a role in determining the clinical phenotype and disease-evolution, most likely because it reflects homozygous or hemizygous mutation. Quantification of the allele burden and the demonstration of homozygous/hemizygous mutation in MPN patients harboring the JAK2 V617F has been conducted using peripheral blood and bone marrow aspirates and cell-free plasma nucleic acid. Variation in the mutation burden of the JAK2V617F has been shown to reflect the size of the myeloproliferative clone, as well as the homozygous/heterozygous state. Homozygosity can be inferred when the percent of JAK2V617F is greater than or equal to 50%. Homozygous JAK2V617F has been observed in 25% of PV patients, while most patients with ET are heterozygous or wild-type. These findings demonstrate the impact that heterozygosity/homozygosity might have on the diverse clinical phenotypes of disease.

Disease monitoring in patients with MPNs has been utilized from bone marrow extractions, peripheral blood, as well as analyzing symptoms. While analysis of tumor samples may not be effective due to numerous constraint such as the difficulty in obtaining tumor samples that may arise, the heterogeneity between tumor localization, and the invasive approach to extract a tumor sample.

A non-invasive method for disease monitoring is through analyzing tumor-derived circulating DNA found in blood plasma. Circulating DNA in blood plasma can be found either as cell-free circulating tumor DNA (ctDNA) or in circulating tumor cells (CTCs). The current understanding is that tumors undergoing necrosis or apoptosis may deposit cell-free fragments of DNA into the bloodstream, which may correlate with prognosis and tumor staging. Common oncogenic DNA mutations have rarely been found in cell-free circulating DNA of healthy individuals, indicating that analyzing ctDNA may be specific to diseased patients.

In patients with MPNs, utilizing blood plasma rather than peripheral blood or bone marrow may be superior for the classification, prognosis, and surveillance of the various disease types. Blood plasma may be more advantageous by being less diluted with normal cell DNA, and more concentrated with tumor-specific nucleic acid, increasing the sensitivity of molecular diagnostics, while being able to be extracted less invasively. Sequencing of plasma samples have been found to be reliable in distinguishing between heterozygosity and homozygosity/hemizygosity for the JAK2 V617F mutant allele while also revealing JAK2 V617F mutants in 7% of patients who were negative by cell analysis.

Fragment length analysis (FLA) is a reliable technique in detecting this type of mutation. Furthermore, FLA allows quantifying the mutant DNA and better evaluation of tumor load. Determining tumor load can be confusing and difficult when the mutation is biallelic. Distinguishing between patients with single allele mutation from those with biallelic mutations might add another dimension in predicting clinical behavior and determining the tumor load.

SUMMARY OF THE INVENTION

According to the invention, cell-free DNA in peripheral blood plasma or serum from a patient suspected of having MPN is tested for CALR mutations and to determine tumor load by using fragment length analysis which can be further combined with direct bidirectional sequencing. Utilizing fragment length analysis (FLA) provides a more efficient approach for the quantification of allele burden compared to traditional Sanger Sequencing.

In one embodiment, the invention comprises a method for screening and/or monitoring a patient for a myeloproliferative neoplasm, the method comprising extracting cell-free DNA from peripheral blood plasma or serum from the patient; performing fragment length analysis of calreticulin human gene (CALR) in the cell-free DNA; and determining tumor load and biallelic mutation in calreticulin human gene (CALR). At least in some embodiments, the fragment length analysis comprises a step of labeling CALR fragments with one or more fluorescent dyes, amplifying the labeled fragments using polymerase chain reaction (PCR), separating the labeled fragments by size using capillary electrophoresis, and analyzing the data using software to determine the size of the amplified labeled fragments and genotype. In some embodiments, the fragment length analysis comprises a step of amplifying a fragment of CALR gene by PCR. In further embodiments, the amplified fragment comprises at least a portion of CALR exon 9. The amplification may be performed with primers specific to CALR exon 9 and with at least one of the primers being labeled with a fluorescent dye. At least some embodiments are performed with the following primers: GGC AAG GCC CTG AGG TGT (SEQ ID NO. 1) and GGC CTC AGT CCA GCC CTG (SEQ ID NO. 2). In other embodiments, any primers specific to CALR and with at least one of the primers being labeled with a fluorescent dye can be used.

Some embodiments include performing the CALR fragment length analysis for a patient who is suspected to have myeloproliferative neoplasm (MPN), but tested negative for mutations in Janus kinase 2 (JAK-2) and myeloproliferative leukemia protein (MPL) genes. In some embodiments, the CALR fragment length analysis can be performed in combination with screening and monitoring for mutations in Janus kinase 2 (JAK-2) and myeloproliferative leukemia protein (MPL).

Further embodiments provide a method of monitoring a patient, the method comprising: obtaining cell-free DNA from peripheral blood plasma or serum of the patient; amplifying a fragment of CALR by a PCR; separating the amplified CALR fragments by size; determining the size of the amplified CALR fragments; and administering a treatment for MPN if the amplified CALR fragments differ in size from a healthy control sample. This method may comprise a step of performing a PCR with primers specific for CALR exon 9. The PCR may be conducted with a composition comprising the primer with SEQ ID NO. 1 and primer with SEQ ID NO. 2. The amplified CALR fragments may be separated by capillary electrophoresis.

Further embodiments include a kit for diagnosing, monitoring and managing a patient with MPN. This kit includes the primer with SEQ ID NO. 1 and primer with SEQ ID NO. 2. The kit is suitable for diagnosing, monitoring and managing an MPN patient suffering from any of the following diseases: chronic myelogenous leukemia, polycythemia vera, primary myelofibrosis, essential thrombocythemia, chronic neutrophilic leukemia and chronic eosinophilic leukemia.

BRIEF DESCRIPTION OF THE DRAWINGS

FIGS. 1A-1C are electropherograms showing the results for normal and biallelic with similar mutations and different mutations, respectively. FIG. 1A is an electropherogram of a normal sample. FIG. 1B is an electropherogram of biallelic similar mutations. FIG. 1C is an electropherogram of biallelic different mutations.

DETAILED DESCRIPTION

Figure 2:
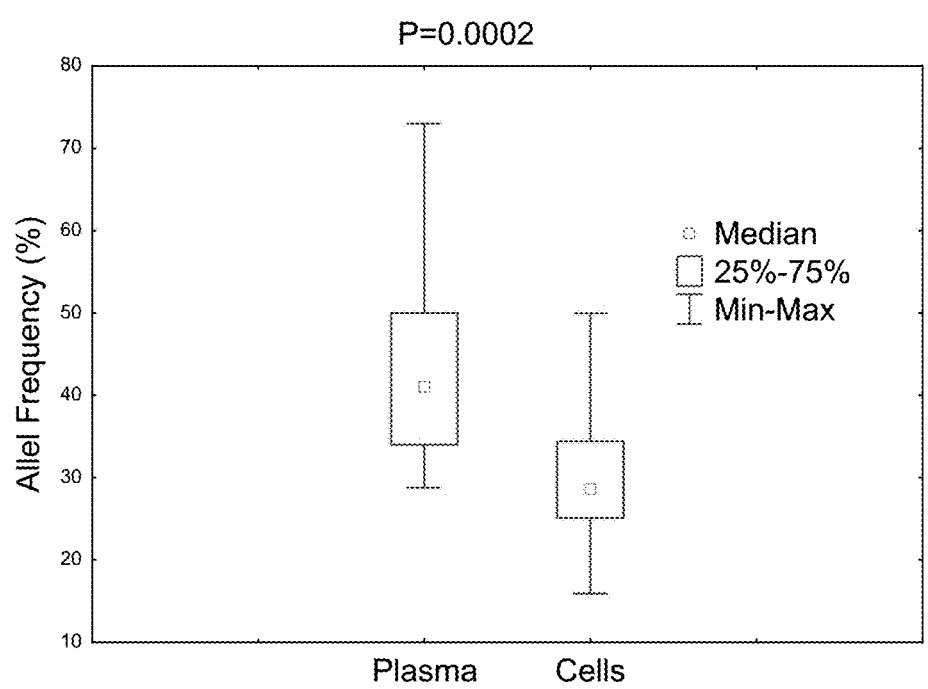
FIG. 2 is a plot comparing allelic mutation frequency detected with cell-free DNA sample from peripheral blood plasma ("Plasma") and cell-based DNA sample ("Cells").

In one embodiment, this invention provides a method for screening and/or monitoring a patient for a myeloproliferative neoplasm comprising extracting cell-free DNA from peripheral blood plasma or serum from the patient; and determining tumor load and biallelic mutation in calreticulin human gene (CALR) by using fragment length analysis, and optionally further by using bidirectional sequencing.

This invention also provides compositions and methods for managing myeloproliferative neoplasms (MPNs). Further embodiments provide compositions and methods for diagnosing myeloproliferative neoplasms (MPNs) and differentiating MPN from a reactive process. Other embodiments provide compositions and methods for monitoring a patient for MPN. Yet further embodiments provide compositions and methods for detecting a CALR mutation and determining tumor load. Other embodiments provide compositions and methods suitable for developing a management plan for MPN and formulating a prognosis report for patient's life expectancy based on whether a CALR mutation has been detected and its allelic frequency.

In these methods, a cell-free DNA sample from patient's peripheral blood plasma or serum is obtained first and then analyzed for somatic mutations in human calreticulin gene (CALR, NCBI GenBank accession number NC_000019, region 12937715 . . . 12945373). In some embodiments, the methods comprise extracting cell-free DNA from peripheral blood plasma or serum sample of a patient and determining tumor load and biallelic mutation in CALR by performing fragment length analysis. This analysis may further comprise sequencing. In some embodiments, the method may comprise bidirectional sequencing of at least a portion of CALR.

In some embodiments, the fragment length analysis comprises a step of isolating cell-free DNA from peripheral blood plasma or serum, labeling CALR fragments with one or more fluorescent dyes, amplifying the labeled fragments by polymerase chain reaction (PCR), separating the labeled fragments by capillary electrophoresis, and analyzing the data using software to determine the size of the amplified fragment. The analysis also allows to distinguish between samples in which only one mutation in CALR is present from samples in which several different mutations are present. This analysis allows to determine a tumor load and whether the CALR mutation is present in both alleles of CALR (biallelic mutation) or only in one allele. This determination of patient's genotype is important for prognosis.

At least some embodiments of the methods are performed with a composition comprising the following CALR primers: GGC AAG GCC CTG AGG TGT (CALRf-DF, SEQ ID NO. 1) and GGC CTC AGT CCA GCC CTG (CALRf-DR, SEQ ID NO. 2). In these embodiments, at least one of primers with SEQ ID NO. 1 and SEQ ID NO. 2 is labeled with a fluorescent dye, and the primers are used to amply a fragment of CALR gene exon 9 by PCR. At least in some embodiments, at least one of the primers is labeled with 6-FAM. In further embodiments, CALR primer with SEQ ID NO. 1 is labeled with 6-FAM. The amplified CALR exon 9 fragments are then analyzed to determine the size of the amplified fragment by capillary electrophoresis.

As shown in FIG. 1A, an electropherogram of CALR exon 9 with no deletion or insertion mutations detects a 260 bp fragment when PCR is performed with primers with SEQ ID NO. 1 and SEQ ID NO. 2. If there is a deletion or insertion in CALR exon 9, the method detects a fragment of different size as shown in FIG. 1B and FIG. 1C. In this method, the intensity of the mutant and wild-type peaks can be used to calculate the mutant rate (semi-quantitation). A sequencing method can be used to determine whether any point mutations are present.

A person of skill will appreciate that a sample in FIG. 1A does not show deletion or insertion mutations in CALR, while a sample in FIG. 1B reveals biallelic similar mutations, and a sample in FIG. 1C reveals biallelic different mutations.

Other embodiments can be performed with at least one forward DNA primer of about 10 to 35 nucleotides long and comprising some sequence of the leading strand of human CALR and at least one reverse primer of about 15 to 30 nucleotides long and comprising some sequence of the lagging strand of human CALR, such that a PCR fragment can be generated from CALR gene, when using the pair of forward and reverse primers.

Other embodiments can be performed with at least one forward DNA primer of about 10 to 35 nucleotides long and comprising some sequence of the leading strand of human CALR exon 9 and at least one reverse primer of about 15 to 30 nucleotides long and comprising some sequence of the lagging strand of human CALR exon 9, such that a PCR fragment can be generated from exon 9 of CALR gene, when using the pair of forward and reverse primers.

While some embodiments include a method in which a patient is screened for one or more mutations in exon 9 of CALR, other embodiments may include a screening for at least one mutation in any position of CALR gene, including, but not limited to, any exon, intron and promoter region.

In the methods of monitoring, management and treatment, a treatment plan can be developed or modified based on whether the fragment length analysis identifies mutations in CALR gene. If one or more CALR mutations are identified, a doctor may determine that a patient is in need of treatment for MPN, including any of the following diseases: chronic myelogenous leukemia, polycythemia vera, primary myelofibrosis, essential thrombocythemia, chronic neutrophilic leukemia and chronic eosinophilic leukemia.

It will be appreciated that the term "CALR mutation" is to be understood broadly and includes point mutations, deletions and insertions. According to the invention, cell-free DNA in peripheral blood plasma or serum from a patient suspected of having MPN is tested for CALR mutations and to determine tumor load using fragment length analysis which may further comprise bidirectional sequencing.

A person of skill will appreciate that the term "treatment" is understood in this disclosure broadly and does not require a complete cure from MPN. The term "treatment" may be used interchangeably with the term "management." Any improvement in patient's condition or any stabilization of the patient's condition is considered to be treatment or management. In addition to stabilizing and/or improving, treatment or management also may include delaying, ameliorating or controlling progression of MPN, even if it does not result in putting the disease into remission.

In some embodiments, treatment or management may include administering to a patient diagnosed as a patient with MPN at least one therapeutic agent selected from blood transfusions, chemotherapeutic agents, radiation therapy and stem cell transplants.

In some embodiments, the fragment length analysis of CALR can be performed in combination with mutation analysis of other genes, such as for example JAK-2 (Janus kinase 2) and MPL (also known as thrombopoietin receptor or MyeloProliferative Leukemia protein).

The methods and compositions of this invention may be used to detect mutations in the CALR gene and/or CALR protein using a biological sample obtained from an individual. The nucleic acid (DNA or RNA) may be isolated from the sample according to any methods well known to those of skill in the art. If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the individual's cells to detect using polymerase chain reaction.

It has been unexpectedly determined that diagnostic tests for mutations in CALR can be performed with high precision and accuracy on cell-free DNA samples obtained from peripheral blood plasma or serum. Either "fresh" blood plasma or serum, or frozen (stored) and subsequently thawed blood plasma or serum may be used. Frozen (stored) plasma or serum should optimally be maintained at storage conditions of −20° C. to −70° C. degrees centigrade until thawed and used. "Fresh" plasma or serum should be refrigerated or maintained on ice until used, with nucleic acid (e.g., RNA, DNA or total nucleic acid) extraction being performed as soon as possible.

It has been also determined that the fragment length analysis detects the presence of low level mutant CALR DNA which was not detectable by sequencing alone. Thus, the present method is suitable for detecting CALR mutations at the low level mutation load.

Comparing ratios of mutant peak (tumor load) between cellular DNA and cell-free DNA in peripheral blood plasma, mutant CALR DNA is significantly higher (P=0.0002, Wilcoxon matched pairs test) in cell-free DNA in peripheral blood plasma than in cellular DNA. As can be seen in the electropherograms of FIGS. 1A-1C, this is apparent when two mutations are different in the length of deletion or insertion.

In the fragment length analysis, the mutant peak is measured as a ratio of the wild-type peak to determine tumor load. The cellular DNA tumor load is compared with that of the cell-free DNA from peripheral blood plasma.

As shown in FIG. 2, mutant CALR DNA is significantly higher (P=0.0002, Wilcoxon matched pairs test) in cell-free DNA in peripheral blood plasma than in cellular DNA reflecting enrichment of the peripheral blood plasma by the tumor-specific DNA.

This allows to determine the presence of a biallelic mutation (a mutation present in both alleles), which is most likely represents more aggressive disease. In this embodiment, any mutant peak that is >55% [(mutant:mutant+ normal)×100] represents a biallelic mutation. In one particular analysis, 5 of 31 (16%) patients when cell-free DNA in peripheral blood plasma was used are presented with a biallelic mutation in CALR. In contrast, only 1 of the same 31 (3%) patients showed evidence of a biallelic mutation when cellular DNA was used. Thus, some technical advantages exist for methods with cell-free DNA from peripheral blood plasma or serum. Most of the mutations (25 of 31, 81%) were deletions. As deletions result in smaller size amplicon on the fragment length analysis and better amplification efficiency, 55% was set as a cut-off for a biallelic mutation to account for the more efficient amplification of the deleted peak.

Cell-free DNA from peripheral blood plasma or serum is more reliable and can quantify the tumor load and determine biallelic (homozygous) mutations more accurately than cellular DNA for detection of CALR mutations and for determining tumor load. Further, using FLA is more sensitive than direct sequencing. These results support a conclusion that using FLA on cell-free peripheral blood plasma DNA is an accurate method for detecting CALR mutations. Using FLA allows the detection of the presence of different mutations that could present biallelic or subclonal variation. The invention will be now explained in more detail through the following non-limiting examples.

EXAMPLE 1

Cell-Free DNA Preparation

Plasma was isolated from peripheral blood samples collected in EDTA anticoagulant by centrifugation at 1000×g for 10-15 min. Total nucleic acid was isolated from plasma using NucliSens extraction kit (bioMerieux Inc., Durham, N.C.) according to the manufacturer's instructions.

EXAMPLE 2

Fragment Length Analysis

PCR/fragment reaction covering CALR gene mutation hot spot exon 9 was performed using a 6-Fam labeled primer. The CALR exon 9 mutated or normal control were verified by determining the size of PCR products using ABI Genetic Analyzer. Normal control specimens displayed a 260 bp peak, while those with mutated CALR (with insertion/deletion) displayed various size peaks in addition to the CALR 260 bp normal control peak. The intensity of the mutant and wild-type peaks can be used to calculate the mutant rate (semi-quantitation).

Tables 1 and 2 below provide reagents and primer sequences, respectively, used in this procedure.

TABLE 1

Laboratory Reagents

| Reagent | Vendor | Catalog No. |
|---|---|---|
| QIAmp DNA Blood Mini Kit | Qiagen | 52302 |
| NucliSens Magnetic Extraction Reagent | Biomerieux | 200293/48 |
| FastStart Taq DNA Polymerase (500rxns) | Roche | 2032937 |
| GeneScan 600 LIZ size standard v2.0 (800rxn) | Applied Biosystems | 4408399 |
| Nuclease Free Water | Fischer Scientific | BP2484-100 or equivalent |
| Ethanol Absolute 200 proof | Sigma | E7023-500ML or equivalent |
| 2% E-gel 96 Agarose, 8/PK | Invitrogen | Cat#G7008-02 |
| Sodium Acetate Buffer, pH 5.2 | Sigma | S7899-500 mL |
| HI-DI Formamide | Applied Biosystems | 4311320 |
| BigDye Terminator v3.1 Cycle Sequencing Kit | Applied Biosystems | 4336917 |
| (3730) POP-7 Polymer | Applied Biosystems | Cat#AB 4335615 |
| ABI running buffer 10X with EDTA | Applied Biosystems | Cat#AB 4335613 |

TABLE 2

CALR primers

| Primer Name | Sequence |
|---|---|
| CALRf-DF | GGC AAG GCC CTG AGG TGT (SEQ ID NO. 1, labeled with 6-FAM at the 5'-end) |
| CALRf-DR | GGC CTC AGT CCA GCC CTG (SEQ ID NO. 2) |

Forward and reverse primers were ordered as 80,000 pmol/vial. 800 μL of RNase free water was added to primers to obtain 100 μM concentration, which was aliquoted to five tubes with appropriate label with primer name, concentration (100 μM) and date. When stored in a −80° C. freezer, primers are stable for at least 2 years after re-constitution. The primers should be re-evaluated after 2 years and the stability extended accordingly.

TABLE 3

Formamide/Liz 600 mixture (loading Mix)

| Reagent | 1 reaction (μL) | 100 reactions (μL) |
|---|---|---|
| Formamide | 9 | 900 |
| LIZ 600 standard | 0.4 | 40 |

PCR reactions were performed at the conditions as listed in Table 4 below.

TABLE 4

Thermal Cycler Conditions

| Step 1: | 95° C. | 6 min |
| Step 2: | 94° C. | 30 sec |
| Step 3: | 56° C. | 30 sec |
| Step 4: | 72° C. | 1.2 min |
| Step 5: | Go To Step 2, 40 times | |
| Step 6: | 72° C. | 10 min |
| Step 7: | 4° C. | Forever |

The mutant DNA peak was quantified and the relative percentage of mutant DNA was calculated in both cellular DNA and cell-free plasma DNA. FLA and Sanger sequencing data were compared for cellular DNA and cell-free plasma DNA. Any ratio >55% was considered as evidence of a biallelic mutation.

This analysis was conducted on samples from 522 patients with consent. Using direct bidirectional sequencing and FLA, CALR insertion/deletion mutations were detected in 71 of 522 (14%) patients suspected of having MPN and referred for testing for CALR mutations. No sample showed a point mutation. DNA from cells and cell-free DNA in peripheral blood plasma was available from 31 of the 71 cases.

To further validate the technical advantage of utilizing peripheral blood plasma rather than peripheral blood or bone marrow for CALR mutation analysis, as well as the technical advantage of FLA over Sanger Sequencing for CALR mutation analysis, the quantification of the CALR mutant allele burden in plasma and cell samples of patients who had undergone the CALR mutation analysis was compared.

All positive samples by cellular DNA testing also showed the indel (insertion/deletion) mutation in cell-free DNA peripheral blood plasma by FLA. The presence of low level (<10%) mutant CALR DNA was not detectable by sequencing, while the FLA was very sensitive in detecting this low level of mutation. This was true whether plasma or cellular DNA was used. Four of the 31 (13%) positive samples by FLA failed to show the mutation on Sanger sequencing. The most likely cause for failing to detect the mutation by Sanger is a low level mutation load and the lower sensitivity of Sanger sequencing.

When ratios of mutant peak (tumor load) were compared between cellular DNA and cell-free DNA in plasma, mutant CALR DNA was significantly higher (P=0.0002, Wilcoxon matched pairs test) in cell-free DNA in plasma than in cellular DNA. Furthermore, when a biallelic mutation is present, determining the presence of this mutation was missed by Sanger, but easily detected by FLA. As can be seen in the electropherograms of FIGS. 1A-1C, this was apparent when the two mutations are different in the length of deletion or insertion.

Based on analyzing FLA, the mutant peak was measured as a ratio of the wild-type peak to determine tumor load. The cellular DNA tumor load was compared with that of the cell-free plasma DNA. Mutant CALR DNA was significantly higher (P=0.0002, Wilcoxon matched pairs test) (see FIG. 2) in cell-free DNA in plasma than in cellular DNA reflecting enrichment of the plasma by the tumor-specific DNA. Thus, this method detects the presence of a biallelic mutation, which is most likely represents more aggressive disease.

Any mutant peak that is >55% [(mutant/mutant+normal)× 100] is considered to represent a biallelic mutation. Based on this, 5 of 31 (16%) patients when cell-free DNA in plasma is used showed biallelic mutation. In contrast, only 1 of 31 (3%) patients showed evidence of biallelic mutation when cellular DNA is used. Most of the mutations (25 of 31, 81%) were deletions. As deletions result in a smaller size amplicon on the FLA and better amplification efficiency, 55% was set as a cut-off for a biallelic mutation to account for more efficient amplification of the peak with a deletion.

Based on these results, cell-free DNA in peripheral blood plasma is more reliable source for determining CALR mutations and it can be used to quantify the tumor load and to determine biallelic mutations more accurately than cellular DNA. Further, using FLA is more sensitive than direct sequencing.

What is claimed is:

1. A method for treating a patient for a myeloproliferative neoplasm (MPN), the method comprising:
   (a) testing the patient by:
      obtaining a sample of peripheral blood plasma from the patient;
      extracting cell-free DNA from the sample;
      performing fragment length analysis of calreticulin human gene (CALR) in the extracted cell-free DNA; and
      determining tumor load and biallelic mutation in calreticulin human gene (CALR); and
   (b) administering an anti-MPN therapeutic agent to the patient.

2. The method of claim 1, wherein the fragment length analysis comprises a step of labeling CALR fragments with one or more fluorescent dyes, amplifying the labeled fragments using polymerase chain reaction (PCR), separating the labeled fragments by size using capillary electrophoresis, and analyzing the data using software to determine the size of the amplified labeled fragments and genotype.

3. The method of claim 1, wherein the fragment length analysis comprises a step of amplifying a fragment of CALR gene by PCR.

4. The method of claim 3, wherein the amplified fragment comprises at least a portion of CALR exon 9.

5. The method of claim 3, wherein the amplification is performed with primers specific to CALR exon 9 and wherein at least one of the primers is labeled with a fluorescent dye.

6. The method of claim 3, wherein the amplification is performed with the following primers: GGC AAG GCC CTG AGG TGT (SEQ ID NO. 1) and GGC CTC AGT CCA GCC CTG (SEQ ID NO. 2).

7. The method of claim 3, wherein the amplification is performed with primers specific to CALR and wherein at least one of the primers is labeled with a fluorescent dye.

8. The method of claim 1, wherein testing further comprises bidirectional sequencing of at least a portion of CALR.

9. The method of claim 1, wherein MTN is selected from the group consisting of chronic myelogenous leukemia, polycythemia vera, primary myelofibrosis, essential thrombocythemia, chronic neutrophilic leukemia and chronic eosinophilic leukemia.

10. The method of claim 1, wherein testing further comprises determining mutations in Janus kinase 2 (JAK-2) and myeloproliferative leukemia protein (MPL).

11. The method of claim 1, wherein the biallelic mutation in CALR is indicated if a mutant peak is at least 55% of a normal control peak.

12. A method of treating a patient for a myeloproliferative neoplasm (MPN), the method comprising:
(a) testing the patient by:
obtaining a sample of peripheral blood plasma from the patient;
extracting cell-free DNA from the sample;
amplifying a fragment of CALR within the cell-free DNA by a PCR;
separating the amplified CALR fragments by size;
determining the size of the amplified CALR fragments;
generating an electropherogram and comparing peak intensities of mutant and wild-type peak to determine a mutation rate, wherein a mutation rate that exceeds a threshold indicates a biallelic mutation in CALR; and
(b) administering a treatment for MPN.

13. The method of claim 12, wherein PCR is conducted with primers specific for CALR exon 9.

14. The method of claim 12, wherein the PCR is conducted with a composition comprising the primer with SEQ ID NO. 1 and primer with SEQ ID NO. 2.

15. The method of claim 12, wherein the amplified CALR fragments are separated by capillary electrophoresis and wherein the amplified fragments are labeled with a fluorescent dye.

16. The method of claim 12, wherein MPN is selected from the group consisting of chronic myelogenous leukemia, polycythemia vera, primary myelofibrosis, essential thrombocythemia, chronic neutrophilic leukemia and chronic eosinophilic leukemia.

17. The method of claim 12, wherein the treatment is selected from the group consisting of blood transfusions, chemotherapeutic agents, radiation therapy and stem cell transplants.

18. The method of claim 1, wherein determining tumor load and biallelic mutation comprises:
generating an electropherogram; and
comparing peak intensities of mutant and wild-type peaks within the electropherogram to determine a mutant rate.

19. The method of claim 12, wherein the threshold is exceeded when the mutant peak is at least 55% of the wild-type peak.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: DNA primer generated in laboratory

<400> SEQUENCE: 1
ggcaaggccc tgaggtgt                                                 18

<210> SEQ ID NO 2
<211> LENGTH: 18
<212> TYPE: DNA
<213> ORGANISM: Artificial Sequence
<220> FEATURE:
<223> OTHER INFORMATION: DNA primer generated in laboratory

<400> SEQUENCE: 2
ggcctcagtc cagccctg                                                 18
```